US005731101A

United States Patent [19]
Sherif et al.

[11] Patent Number: 5,731,101
[45] Date of Patent: Mar. 24, 1998

[54] LOW TEMPERATURE IONIC LIQUIDS

[75] Inventors: Fawzy G. Sherif, Stony Point; Lieh-Jiun Shyu, Yorktown Heights, both of N.Y.; Christine P. M. Lacroix, Twello; Auke G. Talma, Bathmen, both of Netherlands

[73] Assignee: Akzo Nobel NV, Arnhem, Netherlands

[21] Appl. No.: 681,338

[22] Filed: Jul. 22, 1996

[51] Int. Cl.$^6$ ..................... H01M 4/36
[52] U.S. Cl. ............ 429/102; 429/194; 429/198; 429/199; 429/200; 429/206; 429/207; 429/103; 429/104; 252/62.2; 252/182.1; 502/169; 502/200; 502/224; 502/229; 502/230
[58] Field of Search ................ 429/192, 194, 429/198, 199, 200, 206, 207, 102, 103, 104; 252/182.1, 62.2; 502/169, 200, 224, 229, 230

[56] References Cited

U.S. PATENT DOCUMENTS

| | | | |
|---|---|---|---|
| 4,761,164 | 8/1988 | Pez et al. | 55/16 |
| 4,764,440 | 8/1988 | Jones et al. | 429/198 |
| 4,839,249 | 6/1989 | Jones et al. | 429/194 |
| 5,045,244 | 9/1991 | Marlett | 260/665 G |
| 5,104,840 | 4/1992 | Chauvin et al. | 502/117 |
| 5,188,914 | 2/1993 | Blomgren et al. | 429/112 |

FOREIGN PATENT DOCUMENTS

| | | |
|---|---|---|
| 558187 | 9/1993 | European Pat. Off. . |
| 563859 | 10/1993 | European Pat. Off. . |
| 576323 | 12/1993 | European Pat. Off. . |
| 612720 | 8/1994 | European Pat. Off. . |
| WO 95/21806 | 8/1995 | WIPO . |
| WO 95/21871 | 8/1995 | WIPO . |
| WO 95/21872 | 8/1995 | WIPO . |
| WO 96/20905 | 7/1996 | WIPO . |

OTHER PUBLICATIONS

K. Rajeshwar et al., "Room Temperature Molten Salt Electrolytes for Photoelectrochemical Applications", Transactions of the ASME, vol. 104, Aug. 1982, pp. 146–152.

J.R. Silkey et al., "Electrochemical Studies of Triethylammonium Dichlorocuprate (I), A Room Temperature Fused Salt", J. Electrochem. Soc.: Electrochemical Science and Technology, May 1980, vol. 127, No. 5, pp. 1091–1095.

Derwent Patent Abstract No. 94–001445/01 (1994) no month available.

L.A. Kazitsyna, "Structure of the Binary Diazonium Salts [Determined] By a Spectroscopic Method", Tr. Sovesshch. po Fiz. Metodam Issled. Organ. Soedin. I Khim. Protsessov, Akad. Nauk Kirg. SSR. Inst. Organ. Khim., Frunze 1962, 128–136 (Russian), no month available.

Derwent Patent Abstract 88–301632/43 (1988) no month available.

Derwent Patent Abstract 93–360172/46 (1993) no month available.

Derwent Patent Abstract 89–272569/38 (1989) no month available.

M. Matsui et al., "Aluminum Chloride–Tetraalkylammonium Halide Complex as a Novel Catalyst in Friedel–Crafts Alkylation. Direct Construction of the Chroman Structure from 1,3-Diene", Bull. Chem. Soc. Jpn., 68, 2663–2668 (1995), no month available.

Y. Chauvin et al., "Nonaqueous Ionic Liquids as Reaction Solvents", Chemtech, Sep., 1995, 26–30.

*Primary Examiner*—Bruce F. Bell
*Attorney, Agent, or Firm*—Richard P. Fennelly; Louis A. Morris

[57] ABSTRACT

A low temperature molten ionic liquid composition comprising a mixture of a metal halide and an alkyl-containing amine hydrohalide salt is described which is useful as a catalyst and a solvent in alkylation, arylation and polymerization reactions or as an electrolyte for batteries. The metal halide is a covalently bonded metal halide which can contain a metal selected from the group comprised of aluminum, gallium, iron, copper, zinc, and indium, and is most preferably aluminum trichloride. The alkyl-containing amine hydrohalide salt may contain up to three alkyl groups, which are preferably lower alkyl, such as methyl and ethyl.

14 Claims, No Drawings

LOW TEMPERATURE IONIC LIQUIDS

BACKGROUND OF THE INVENTION

This invention relates to compositions which are molten at low temperatures which are suitable, for example, for use as a catalyst and as a solvent in alkylation and polymerization reactions as well as in dimerization, oligomerization acetylation, metatheses, and copolymerization reactions.

A class of ionic liquids which is of special interest is the class of fused salt compositions which are molten at low temperature and are useful as catalysts, solvents and electrolytes. Such compositions are mixtures of components which are liquid at temperatures below the individual melting points of the components. The mixtures can form molten compositions simultaneously upon contacting the components together, or after heating and subsequent cooling.

Examples of such low temperature ionic liquids or molten fused salts are the chloroaluminate salts discussed by J. S. Wilkes, et al., J. Inorg. Chem., Vol. 21, 1263–1264, 1982. Alkyl imidazolium or pyridinium salts, for example, can be mixed with aluminum trichloride ($AlCl_3$) to form the fused chloroaluminate salts. Also, chlorogallate salts made from gallium trichloride and methylethyl-imidazolium chloride are discussed in Wicelinski et al., "Low Temperature Chlorogallate Molten Salt Systems," J. Electrochemical Soc., Vol. 134, 262– 263, 1987. The use of the fused salts of 1-alkylpyridinium chloride and aluminum trichloride as electrolytes are discussed in U.S. Pat. No. 4,122,245. Other patents which discuss the use of fused salts from aluminum trichloride and alkylimidazolium halides as electrolytes are U.S. Pat. Nos. 4,463,071 and 4,463,072 and British Patent No. 2,150,740. Unfortunately, the alkylimidazolium salts are difficult to prepare, and the alkyl pyridinium salts can be too easily reduced.

U.S. Pat. No. 4,764,440 to S. D. Jones describes ionic liquids which comprise a mixture of a metal halide, such as aluminum trichloride, and what is termed a "hydrocarbyl-saturated onium salt", such as trimethylphenylammonium chloride. In such ionic liquids, the onium salt component, if based on the presence of a nitrogen atom, is fully saturated with four substituent groups.

U.S. Pat. No. 5,104,840 to Y. Chauvin et al. describes ionic liquids which comprise at least one alkylaluminum dihalide and at least one quaternary ammonium halide and/or at least one quaternary ammonium phosphonium halide; and their uses as solvents in catalytic reations.

PCT International Patent Publication No. WO 95/21872 describes ternary ionic liquids which can comprise a metal halide, such as aluminum trichloride, an imidazolium or pyridinium halide, and a hydrocarbyl substituted quaternary ammonium halide or a hydrocarbyl substituted phosphonium halide. See page 4, lines 18–24 for the description of the hydrocarbyl substituted quaternary ammonium halide.

In view of the disadvantages of known compositions, it would be desirable to have fused salt compositions which would not be difficult to prepare, which would be useful, for example, as a catalyst in alkylation and polymerization reactions and as solvents for chemical and electrochemical processes, and which would be formed using relatively low cost components as compared to the ionic liquids of the prior art.

SUMMARY OF THE INVENTION

This invention is a low temperature molten composition comprising a mixture of a metal halide and an alkyl-containing amine hydrohalide salt. The compositions of this invention provide fused salt low temperature molten compositions, or ionic liquids, which are useful as catalysts and solvents, as described above, and which also have utility as electrolytes in batteries, electrorefining processes, and electrowinning processes.

DETAILED DESCRIPTION OF THE INVENTION

The low temperature molten compositions, or ionic liquids, of this invention can be referred to as fused salt compositions, or ionic aprotic solvents. By "low temperature molten" is meant that the compositions are in liquid form below about 100° C. at standard pressure. Preferably, the molten composition is in liquid form below about 60° C., and more preferably below about 30° C. at standard pressure.

The metal halides useful in this invention are those compounds which can form anions containing polyatomic chloride bridges in the presence of the alkyl-containing amine hydrohalide salt. Preferred metal halides are covalently bonded metal halides. Suitable metals which can be selected for use herein include those from Groups VIII and IB and IIB of the Periodic Table of the Elements. Especially preferred metals are selected from the group comprising aluminum, gallium, iron, copper, zinc, and indium, with aluminum being most preferred. The corresponding most preferred halide is chloride and therefore, the most preferred metal halide is aluminum trichloride. This compound is most preferred because it is readily available and can form the polynuclear ion $Al_2Cl_7^-$. Furthermore, the molten compositions comprising this polynuclear ion are useful as described hereinbefore. Mixtures of more than one of these metal halides can be used.

The terminology "alkyl-containing amine hydrohalide salt", as used herein, is intended to cover monoamines, as well as diamines, triamines, other oligoamines and cyclic amines which comprises one or more "alkyl" groups and a hydrohalide anion. The term "alkyl" is intended to cover not only conventional straight and branched alkyl groups of the formula $—(CH_2)_nCH_3$ where n is from 0 to about 29, preferably 0 to about 17, in particular 0 to 3, but other structures containing heteroatoms (such as oxygen, sulfur, silicon, phosphorus, or nitrogen). Such groups can carry substituents. Representative structures include ethylenediamine, ethylenetriamine, morpholino, and poloxyalkylamine substituents. "Alkyl" includes "cycloalkyl" as well.

The preferred alkyl-containing amine hydrohalide salts useful in this invention have at least one alkyl substituent and can contain as many as three alkyl substituents. They are distinguishable from quaternary ammonium salts which have all four of their substituent positions occupied by hydrocarbyl groups. The preferred compounds that are contemplated herein have the generic formula $R_3N.HX$, where at least one of the "R" groups is alkyl, preferably alkyl of from one to eight carbon atoms (preferably, lower alkyl of from one to four carbon atoms) and X is halogen, preferably chloride. If each of the three R groups is designated $R_1$, $R_2$ and $R_3$, respectively, the following possiblities exist in certain embodiments: each of $R_1$–$R_3$ can be lower alkyl optionally interrupted with nitrogen or oxygen or substituted with aryl; $R_1$ and $R_2$ can form a ring with $R_3$ being as previously described for $R_1$; $R_2$ and $R_3$ can either be hydrogen with $R_1$ being as previously described; or $R_1$, $R_2$ and $R_3$ can form a bicyclic ring. Most preferably, these

3 groups are methyl or ethyl groups. If desired the di- and trialkyl species can be used. One or two of the R groups can be aryl, but this is not preferred. The alkyl groups, and aryl, if present, can be substituted with other groups, such as a halogen. Phenyl and benzyl are representative examples of possible aryl groups to select. However, such further substitution may undesirably increase the size of the group, and correspondingly increase the viscosity of the melt. Therefore, it is highly desirable that the alkyl groups, and aryl, if present, be comprised of carbon and hydrogen groups, exclusively. Such short chains are preferred because they form the least viscous or the most conductive melts. Mixtures of these alkyl-containing amine hydrohalide salts can be used.

The mole ratio of alkyl-containing amine hydrohalide salt to metal halide can, in general, range from about 1:1 to about 1:2. In a highly preferred embodiment, the low temperature molten composition of this invention consists essentially of the metal halide and the alkyl-containing amine hydrohalide salt.

Specifically, the most preferred low temperature molten composition is a mixture consisting essentially of a mole ratio of trimethylamine hydrochloride to aluminum trichloride of about 1:2.

Typically, the metal halide and the alkyl-containing amine hydrohalide salt are solids at low temperature, i.e., below about 100° C. at standard pressure. After mixing the two solids together, the mixture can be heated until the mixture becomes a liquid. Alternatively, the heat generated by the addition of the two solids will result in forming a liquid without the need for additional external heating. Upon cooling, the mixture remains a liquid at low temperature, i.e., below about 100° C., preferably below about 60° C., and more preferably below about 23° C.

The following Examples are illustrations and not limitations of the invention.

EXAMPLE 1

Two moles of aluminum trichloride (266.7 g) were added slowly to one mole of stirred trimethylamine hydrochloride salt (95.57 g), both from Aldrich Chemical Co., under a blanket of dry air. The reaction was exothermic. A light brown liquid was formed. This liquid was stirred for one hour, and the liquid had a density of 1.4–1.5 g/cc at room temperature. The product was stable as a liquid at room temperature under a dry atmosphere. When cooled, it changed to a glassy viscous mass at −10° C. On warming to room temperature, it changed back to a flowable liquid.

EXAMPLE 2

This Example is similar to Example 1 with the exception that the experiment was scaled up using a commercially available 70% aqueous solution of trimethylamine hydrochloride (Akzo Nobel Chemicals Inc.). A 200 g portion of the solution (170 cc) was evaporated in a porcelain dish until 60% of the liquid had evaporated. The slurry that formed was then introduced into a flask and was treated with low vacuum using an aspirator until all of the moisture had been removed. The solid was then mixed with two mole equivalents of aluminum trichloride it two steps. Half of the aluminum trichloride was slowly added with stirring. An exotherm occurred, and a brown liquid was formed. The second half of the aluminum trichloride was then added, and a final liquid was formed which stayed liquid at room temperature. The product was analyzed for its elemental composition. It had the formula $(CH_3)_3NH \cdot Al_2Cl_7$. The results of the analysis are as follows: % Al–14.65% (Found), 14.90% (Calculated); % Cl–67.5% (Found), 68.53% (Calculated); % C–10.1% (Found), 9.94% (Calculated); % H–1.0% (Found), 2.76% (Calculated); and % N–4.0% (Found), 3.87% (Calculated). The nuclear magnetic resonance spectra of aluminum showed that the aluminum was present as the heptachloroaluminate anion.

EXAMPLE 3

This Example illustrates the alkylation of benzene to produce cumene using the ionic liquid made in Example 1.

Benzene (24 g) was added into a 3-neck flask equipped with a thermometer and a magnetic stirrer. Nitrogen was continuously introduced into the flask, and 5.65 g of the ionic liquid made in Example 1 was added. The liquids were stirred thoroughly. Propylene gas was bubbling through the liquids at a rate of 60 cc/min. The temperature increased from 26° C. to 62° C. in fifteen minutes. A sample of the benzene layer was taken and analyzed by GC/mass spec, and the results are shown below:

| | |
|---|---|
| $C_6H_6$ | 36% |
| $C_6H_5C_3H_7$ | 50% |
| $C_6H_4(C_3H_7)_2$ | 13% |
| $C_6H_3(C_3H_7)_3$ | 1% |

It can be seen from the previous data that selectivity to cumene formation was high, namely 78%.

EXAMPLE 4

Into an autoclave were loaded 14.8 g of the aluminum trichloride-trimethylammonium ionic liquid from Example 1 and 0.9 g of 2-butene. The autoclave was immersed in an ethylene glycol/dry ice bath at −15° C. The autoclave was removed from the ice bath, and the liquids were stirred thoroughly. The temperature increased to 80° C. due to the exothermic reaction, and the pressure was about 40 psi. The reaction was allowed to run for six hours. The product was a clear organic liquid containing 5% $C_8$, 16% $C_9$, 11% $C_{10}$, 16% $C_{11}$, and 51% alkanes with a carbon number greater than 11.

EXAMPLE 5

This Example shows the alkylation of benzene to produce linear fatty alkyl benzene using the ionic liquid made in Example 1.

Five grams of dodecene and 30 g of benzene were weighed into a 3-neck flask. The liquids were heated to 80° C. in a nitrogen atmosphere. A few samples were withdrawn before (time 0) and after the addition of 0.04 g of the ionic liquid made in Example 1. The samples were analyzed by GC and the results are shown below:

| SAMPLE | TIME (MIN) | $C_6H_6$ | DODECENE | $C_6H_5-C_{12}$ |
|---|---|---|---|---|
| A | 0 | 85.7 | 14.3 | 0 |
| B | 1 | 65.6 | 6.2 | 28.6 |
| C | 15 | 62.9 | 0.1 | 36.2 |
| D | 60 | 72.3 | 0 | 27.6 |

The conversion of dodecene at 80° C. in the excess of benzene was 100% after fifteen minutes of reaction. After sixty minutes, the selectivity to dodecyl benzene was 100%.

EXAMPLE 6

This Example shows the alkylation of toluene with oleonitrile to produce tolylstearonitrile using the ionic liquid made in Example 1.

Into a 250 ml flask was added 40 g of the ionic liquid made in Example 1 (0.11 mole) and 100 ml of toluene. To this was added 29 g of oleonitrile (0.11 mole) over a twenty minute period at room temperature. After the addition, the reaction was heated to 80° C. and was maintained at this temperature for three hours. The reaction was distilled to remove excess toluene. Then, 250 ml. of heptane was added with vigorous stirring. The layers that formed were separated (heptane layer on top and ionic layer on the bottom). The heptane layer was washed with water and was then distilled to collect the product as an undistillable residue. The residue was analyzed to be the desired product, tolylstearonitrile, in 70% yield and 80% purity. The ionic liquid layer was treated with 7.3 g of aluminum chloride (0.055 mole) and was used again in the same reaction with fresh oleonitrile and toluene. Workup by the same procedure, as described above, resulted in a yield of 54% for the desired product (tolylstearonitrile).

EXAMPLE 7

An ionic liquid comprising triethylamine hydrochloride and aluminum trichloride was prepared by introducing triethylamine hydrochloride(2.3 g, 16.7 mmol) into a flask and then introducing the aluminum trichloride (4.4 g, 33.4 mmol) from a dosing funnel. The reaction mixture immediately became sticky and, when approximately 50% of the aluminum trichloride had been added, it became completely fluid and brownish in color. The reaction was exothermic, and the temperature was kept at 30° C. with the use of an ice bath. When all of the aluminum trichloride had been added, the product was slightly brownish in color and remained fluid at room temperature. The ionic liquid stayed in fluid liquid form until cooled to 0° C. at which point it started to become a viscous composition and eventually a glassy material (at about −20° C.).

EXAMPLE 8

Another ionic liquid was formed by introducing dibutylamine hydrochloride (2.5 g, 15.1 mmol) into a flask and then introducing the aluminum trichloride (4.0 g, 30.0 mmol) from a dosing funnel. The reaction mixture immediately became sticky and, when approximately 50% of the aluminum trichloride had been added, it became completely fluid and brownish in color. The reaction was exothermic, and the temperature was kept at 30° C. with the use of an ice bath. When all of the aluminum trichloride had been added the product was slightly brownish in color and remained fluid at room temperature. The ionic liquid stayed in fluid liquid form until cooled to 0° C. at which point it started to become a viscous composition and eventually a glassy material (at about −20° C.).

EXAMPLE 9

Yet another ionic liquid was formed by introducing ethylamine hydrochloride (3.0 g, 36.8 mmol) into a flask and then introducing the aluminum trichloride (9.8 g, 73.6 mmol) from a dosing funnel. The reaction mixture became sticky when approximately 50% of the aluminum trichloride had been added. When all of the aluminum trichloride had been added the product was completely fluid and brownish in color. The reaction was exothermic, and the temperature was kept at 40° C. with the use of an ice bath. The mixture solidified below 35° C.

EXAMPLE 10

Yet another ionic liquid was formed by introducing dibutylamine hydrochloride (2.4 g, 14.6 mmol) into a flask and then introducing ferric trichloride (4.7 g, 29.2 mmol) from a dosing funnel. The reaction mixture immediately became sticky and, when approximately 50% of the ferric trichloride had been added, it was completely fluid and deep brown to black in color. The reaction was exothermic. When all of the ferric trichloride had been added, the product was brown/black in color and solidified below 45° C.

EXAMPLE 11

This Example is similar to Example 1, except that the metal halide was $FeCl_3$. When 9.6 g of trimethylammonium chloride, 0.1 mole, was mixed with 32.4 g of $FeCl_3$ (0.2 mole) and warmed to 40° C., a reaction took place accompanied by an exotherm to about 70° C. A liquid was formed. The liquid was viscous at room temperature but very flowable above 50° C.

EXAMPLE 12

This Example is similar to Example 1, except that the metal halide was $ZnCl_2$. When 9.6 g of trimethylammonium chloride, 0.1 mole, was mixed with 27.2 g of $ZnCl_2$, 0.2 mole, and heated to 100° C., a transparent colorless liquid was formed. Below this temperature, the material was transformed to a transparent glassy solid.

EXAMPLE 13

This Example is similar to Example 1, except that the metal halide was CuCl. When 9.6 g of trimethylammonium chloride, 0.1 mole, was mixed with 19.8 g of CuCl, 0.2 mole, and heated to 50° C., a brown liquid was formed. The material stayed as a liquid above this temperature.

COMPARATIVE EXAMPLE 14

This Example is similar to Example 1 except that the metal halide used was antimony pentachloride. When 9.6 g of trimethylammonium chloride, 0.1 mole, was mixed with 59.8 g of $SbCl_5$, 0.2 mole, and heated to 70° C., no reaction took place, and no liquid was formed.

COMPARATIVE EXAMPLE 15

This Example is similar to Example 1, except the metal chloride was tin tetrachloride, $SnCl_4$. When 9.6 g of trimethylammonium chloride, 0.1 mole, was mixed with 52.1 g of $SnCl_4$, 0.2 mole, no liquid was formed. Upon heating to 70° C., no reaction took place, and no liquid was formed.

COMPARATIVE EXAMPLE 16

This Example is similar to Example 1, except that the metal chloride was nickel chloride, $NiCl_2$. When 9.6 g of trimethylammonium chloride, 0.1 mole, was mixed with 25.9 g of $NiCl_2$, 0.2 mole, no liquid was formed, even after heating to 70° C.

EXAMPLE 17

This Example demonstrates the alkylation of phenol with propylene to form isopropylphenols using the ionic liquid described in Example 1.

Phenol (1 g) was added to a 3-neck flask, and the flask was immersed in an ethanol/dry ice bath at −50° C. Then, 9.6 g of the ionic liquid made in Example 1 was added. The flask was heated to a temperature of 60° C. while propylene was being introduced into the flask at a rate of 125 cc/min. The reaction was allowed to run for three hours. The final product, analyzed by GC/mass spec, is given below:

Phenol: 79%

Isopropyl phenol: 17% (o-isopropyl phenol: 12.5%; m- and p-isopropyl phenol: 4.4%)

Di-isopropyl phenol: 3%

Tri-isopropyl phenol: <0.1%

The conversion of phenol was 21%, and the selectivity to isopropyl phenol was 81%.

EXAMPLE 18

This Example illustrates the oligomerization of propylene using the ionic liquid described in Example 1.

In this Example, 30 g of the ionic liquid made in Example 1 was added to a 3-neck 100 ml flask, the flask was immersed in an ice bath at 0° C., and the ionic liquid was stirred thoroughly. Propylene was then introduced continuously at a flow rate of 15 cc/min for two hours. A clear organic liquid was formed above the ionic liquid layer. This product was analyzed by GC, and the results are shown below:

$C_4$: 2.3%

$C_5$: 2.4%

$C_6$: 2.3%

$C_7$: 89.7%

$C_8$: 3.3%

EXAMPLES 19–21

These Examples illustrate the attempts at the preparation of a basic ionic liquid, a neutral ionic liquid, and an acidic ionic liquid. Only the acidic material was obtainable.

In all the preparations, a three necked round bottom flask (50 mL) equipped with a nitrogen inlet and outlet, a thermometer and a dropping funnel with a large dosing opening, and a magnetic stirring bar were employed. All operations were carried out under a nitrogen atmosphere.

"Basic Ionic Liquid"

Dimethylamine hydrochloride (2.07 g, 25.4 mmol) was introduced into the flask, and $AlCl_3$(1.7 g, 12.7 mmol) was added from the dropping funnel. When all the $AlCl_3$ had been added, the reaction mixture became light brown and sticky. The flask which contained the product mixture was placed in an oil bath and warmed slowly. When the temperature of the oil bath was above the 120° C., HCl gas was formed, and the product decomposed. No ionic liquid was formed using these concentrations of the reagents and these conditions.

"Neutral Ionic Liquid"

Dimethylamine hydrochloride (2.06 g, 25.4 mmol) was introduced into the flask, and $AlCl_3$(3.3 g, 24.7 mmol) was added from the dropping funnel. The addition of $AlCl_3$ was done rapidly, and the reaction was exothermic. When all the $AlCl_3$ had been added, the reaction mixture became light brown and liquid. When the reaction mixture was cooled to room temperature, it became a solid. The melting point of the reaction mixture was measured and was found to be 88° C.

"Acid Ionic Liquid"

Dimethylamine hydrochloride (1.96 g, 24 mmol) was introduced into the flask, and $AlCl_3$(6.5 g, 48.8 mmol) was added from the dropping funnel. The addition of $AlCl_3$ was done rapidly, and the reaction was exothermic. When all the $AlCl_3$ had been added, the reaction mixture became light brown and liquid. When the reaction mixture was cooled to room temperature, it became a solid. The melting point of the reaction mixture was measured and was found to be 34° C.

COMPARATIVE EXAMPLE 19

In this Example, 0.9 g of aluminum trichloride was added into a 50 ml 3-neck flask equipped with a thermometer and a magnetic stirrer which contained 5 mL of cyclohexane. Isobutene was bubbled through the stirred solution. The mixture became a slightly yellow. The reaction mixture was maintained at 20° C. with the use of an ice bath. After ninety minutes, the isobutene flow was stopped. The reaction mixture was quenched with 25 ml of water, and the polymer layer was separated, dried with magnesium sulfate and filtered, yielding a colorless viscous polymer. This polymer was analyzed by HP-SEC (high performance size exclusion chromatography), and the polymer characteristics were as follows: $M_w$(molecular weight average): 5080; $M_n$(number average molecular weights): 1040; and D polydispersity index, $M_w/M_n$): 4.8.

EXAMPLE 20

In this Example, an ionic liquid of ethylamine hydrochloride and aluminum trichloride was prepared in a 30 ml 3-neck flask by adding 1.92 g of aluminum trichloride to 0.58 g of the amine salt. The ionic liquid was slightly brownish in color. The mixture was warmed to 35° C. with an external water bath to keep the mixture fluid. Then, isobutene was bubbled through the stirred ionic liquid. The mixture became yellow. The reaction mixture was maintained at 30° C. with the use of an ice bath. After ninety minutes, the isobutene flow was stopped. The reaction mixture consisted of two layers: a deep yellow lower layer of approximately 2 ml of ionic liquid, and a pale yellow viscous upper layer of some 20 ml of polyisobutene. The reaction mixture was quenched with 25 ml of water, and the polymer layer was separated, dried with magnesium sulfate and filtered, yielding a slightly yellowish viscous polymer. This polymer was analyzed by HP-SEC, and the polymer characteristics were as follows: $M_w$: 1407; $M_n$: 815; and D: 1.73.

EXAMPLE 21

In this Example, an ionic liquid of dibutylamine hydrochloride and aluminum trichloride was prepared in a 50 ml 3-neck flask by adding 1.55 g of aluminum trichloride to 0.95 g of the amine salt. The ionic liquid was slightly brownish in color. The mixture was cooled to 0° C. with an external ice bath. Then, isobutene was bubbled through the stirred ionic liquid. The mixture became yellow, and the temperature rose to approximately 30° C. The reaction mixture was maintained at this temperature with the use of an ice bath. After ninety minutes, the isobutene flow was stopped. The reaction mixture consisted of two layers: a deep yellow lower layer of approximately 2 ml of ionic liquid, and a pale yellow viscous upper layer of some 20 ml of polyisobutene. The reaction mixture was quenched with 25 ml of water, and the polymer layer was separated, dried with magnesium sulfate and was filtered, yielding a slightly yellowish viscous polymer. This polymer was analyzed by HP-SEC, and the polymer characteristics were as follows: $M_w$: 1299; $M_w$: 685; and D: 1.90.

EXAMPLE 22

In this Example, an ionic liquid of diethylamine hydrochloride and aluminum trichloride was prepared in a 50 ml 3-neck flask by adding 1.65 g of aluminum trichloride to 0.85 g of the amine salt. The ionic liquid was slightly brownish in color. The mixture was cooled to 0° C. with an external ice bath. Then, isobutene was bubbled through the stirred ionic liquid. The mixture became yellow, and the temperature rose to approximately 30° C. The reaction mixture was maintained at this temperature with the use of an ice bath. After ninety minutes, the isobutene flow was stopped. The reaction mixture consisted of two layers: a deep yellow lower layer of approximately 2 ml of ionic liquid, and a pale yellow viscous upper layer of some 20 ml of polyisobutene. The reaction mixture was quenched with 25 ml of water, and the polymer layer was separated, dried with magnesium sulfate and was filtered, yielding a slightly yellowish viscous polymer. This polymer was analyzed by HP-SEC, and the polymer characteristics were as follows: $M_w$: 1444; $M_n$: 662; and D: 2.18.

COMPARATIVE EXAMPLE 23

In this Example, 0.3 g of aluminum trichloride was added into a 50 ml 3-neck flask equipped with a thermometer and a magnetic stirrer which contained 30 mL of cyclohexane. A solution of 10 g of styrene in 25 ml of cyclohexane was dosed in twenty-five minutes to the stirred solution. The mixture became yellow, and the temperature started to increase. The reaction mixture was maintained at 25° C. with the use of an ice bath. After fifteen minutes, the reaction mixture was quenched with 25 ml of water, and the organic layer was separated, dried with magnesium sulfate to yield 10 g of a colorless solid brittle, polymer. This polymer analyzed by HP-SEC, and the polymer characteristics were as follows: $M_w$: 1095; $M_n$: 422; and D: 2.6.

EXAMPLE 24

In this Example, an ionic liquid of dibutylamine hydrochloride and aluminum trichloride was prepared in a 50 ml 3-neck flask by adding 0.64 g (4.80 mmol) of aluminum trichloride to 0.41 g (2.42 mmol) of the amine salt. The ionic liquid was slightly brownish in color, and 30 ml of cyclohexane was added to it. A solution of 10 g of styrene in 25 ml of cyclohexane was dosed in twenty-five minutes to the stirred solution. The mixture became yellow, and the temperature began to increase. The reaction mixture was maintained at 20° C. with the use of an ice bath. After fifteen minutes, the reaction mixture was quenched with 25 ml of water, and the polymer layer was separated, dried with magnesium sulfate and filtered, yielding 10 g of a colorless solid, brittle, polymer. This polymer was analyzed by HP-SEC, and the polymer characteristics were as follows: $M_w$: 3785; $M_n$: 650; and D: 5.81.

EXAMPLE 25

In this Example, an ionic liquid of dibutylamine hydrochloride and aluminum trichloride was prepared in a 50 ml 3-neck flask by adding 0.32 g (2.42 mmol) of aluminum trichloride to 0.41 g (2.42 mmol) amine salt. The ionic liquid was slightly brownish, and 30 ml of cyclohexane was added to it. A solution of 10 g of styrene in 25 ml of cyclohexane was dosed in twenty-five minutes to the stirred solution. The mixture became yellow, and the temperature began to increase. The reaction mixture was maintained at 25° C. with the use of an ice bath. After fifteen minutes, the reaction mixture was quenched with 25 ml of water, and the polymer layer was separated, dried with magnesium sulfate and filtered, yielding 10 g of a colorless solid polymer.

The preceding Examples are presented for illustrative purposes only and, for that reason, should not be construed in a limiting sense. The scope of protection sought is set forth in the claims which follow.

We claim:

1. A low temperature molten ionic liquid composition comprising a mixture of a metal halide and an alkyl-containing amine hydrohalide salt of the formula $R_3N.HX$, where at least one R is alkyl and X is halogen, which amine hydrohalide salt contains either one or two alkyl groups therein.

2. The composition of claim 1 wherein the metal halide is a covalently bonded metal halide.

3. The composition of claim 2 wherein the metal of the metal halide is selected from the group comprised of aluminum, gallium, iron, copper, zinc, and indium.

4. The composition of claim 3 wherein the metal halide is aluminum trichloride.

5. The composition of claim 1 which consists essentially of a mole ratio of the chloride of the alkyl-containing amine hydrohalide salt to aluminum trichloride of from about 1:1 to about 1:2.

6. The composition of claim 1 wherein the metal halide contains a metal which is selected from Group VIII, Group IB and Group IIB of the Periodic Table of The Elements.

7. The composition of claim 6 wherein the metal halide is ferric trichloride.

8. A process for forming a low temperature molten ionic liquid composition, comprising a mixture of a metal halide and an alkyl-containing amine hydrohalide salt, which comprises mixing together a solid halide and a solid alkyl-containing amine hydrohalide salt of the formula $R_3N.HX$, where at least one R is alkyl and X is halogen, which amine hydrohalide salt contains either one or two alkyl groups therein.

9. The process of claim 8 wherein the metal halide is a covalently bonded metal halide.

10. The process of claim 9 wherein the metal of the metal halide is selected from the group comprised of aluminum, gallium, iron, copper, zinc, and indium.

11. The process of claim 10 wherein the metal halide is aluminum trichloride.

12. The process of claim 8 which consists essentially of a mole ratio of the chloride of the alkyl-containing amine hydrohalide salt to aluminum trichloride of from about 1:1 to about 1:2.

13. The process of claim 8 wherein the metal halide contains a metal which is selected from Group VIII, Group IB and Group IIB of the Periodic Table of The Elements.

14. The composition of claim 13 wherein the metal halide is ferric trichloride.

* * * * *